US009950090B2

(12) United States Patent
Mayor Sans et al.

(10) Patent No.: US 9,950,090 B2
(45) Date of Patent: Apr. 24, 2018

(54) SYSTEM FOR RELEASING VOLATILE SUBSTANCES

(71) Applicant: ZOBELE ESPAÑA, S.A., Barcelona (ES)

(72) Inventors: Fernando Mayor Sans, Barcelona (ES); Elisabeth Martinez De Morentin Pujabet, Barcelona (ES); Joaquim Llorente Alonso, Barcelona (ES)

(73) Assignee: ZOBELE ESPAÑA, S.A., Barcelona (ES)

( * ) Notice: Subject to any disclaimer, the term of this patent is extended or adjusted under 35 U.S.C. 154(b) by 0 days.

(21) Appl. No.: 15/106,255

(22) PCT Filed: Dec. 16, 2014

(86) PCT No.: PCT/ES2014/070927
§ 371 (c)(1),
(2) Date: Jun. 17, 2016

(87) PCT Pub. No.: WO2015/092103
PCT Pub. Date: Jun. 25, 2015

(65) Prior Publication Data
US 2017/0000920 A1 Jan. 5, 2017

(30) Foreign Application Priority Data
Dec. 19, 2013 (ES) .................................. 201331874

(51) Int. Cl.
*A61L 9/12* (2006.01)
*B01F 3/04* (2006.01)

(52) U.S. Cl.
CPC ................. *A61L 9/122* (2013.01); *A61L 9/12* (2013.01); *B01F 3/04* (2013.01); *A61L 2209/11* (2013.01)

(58) Field of Classification Search
CPC ............... A61L 9/12; A61L 9/122; B01F 3/04
(Continued)

(56) References Cited

U.S. PATENT DOCUMENTS 9,265,853 B2 * 2/2016 Scott ....................... A61L 9/122
2002/0197188 A1 12/2002 Lua
(Continued)

FOREIGN PATENT DOCUMENTS

DE 20211634 U1 1/2003
DE 10 2005 032418 B3 4/2007
(Continued)

OTHER PUBLICATIONS

International Search Report received in PCT Patent Application No. PCT/ES2014/070927 dated Feb. 19, 2015 in 4 pages.
(Continued)

*Primary Examiner* — Robert A Hopkins
(74) *Attorney, Agent, or Firm* — Knobbe, Martens, Olson & Bear, LLP

(57) ABSTRACT

A system for releasing volatile substances includes a receptacle housing a volatile substance, a ventilation surface arranged in the receptacle provided with ventilation windows, and a fan for inducing the ventilation of the scent of the volatile substance. The fan can move between at least two positions. The effectiveness with which the perfume evaporates during the work cycle of the device can be improved and controlled with the system.

9 Claims, 2 Drawing Sheets

(58) Field of Classification Search
USPC .............................. 261/30, DIG. 88; 239/34
See application file for complete search history.

(56) References Cited

U.S. PATENT DOCUMENTS

2009/0162253 A1    6/2009  Porchia
2013/0328223 A1   12/2013  Sharma et al.

FOREIGN PATENT DOCUMENTS

| EP | 1252900 A1 | 10/2002 |
| EP | 1586335 A1 | 10/2005 |
| EP | 2 409 716 A2 | 1/2012 |
| EP | 2 409 716 A3 | 1/2012 |
| EP | 2409716 A2 | 1/2012 |
| WO | WO 02/100449 A1 | 12/2002 |

OTHER PUBLICATIONS

Supplementary European Search Report dated Aug. 2, 2017 in European Patent Application No. EP 14 87 0912.

* cited by examiner

SYSTEM FOR RELEASING VOLATILE SUBSTANCES

INCORPORATION BY REFERENCE TO ANY PRIORITY APPLICATIONS

This application is the U.S. National Phase of International Application No. PCT/ES2014/070927, filed Dec. 16, 2014, designating the U.S. and claiming priority to European Application No. P201331874, filed Dec. 19, 2013. Any and all applications for which a foreign or domestic priority claim is identified here or in the Application Data Sheet as filed with the present application are hereby incorporated by reference under 37 CFR 1.57.

FIELD OF THE INVENTION

The present invention relates to a system for releasing volatile substances, comprising a fan for generating an airflow with a scent generated by a volatile substance.

BACKGROUND OF THE INVENTION

A type of air fresheners or systems for releasing volatile substances known today is formed by a receptacle or container housing an air freshening product or a volatile substance.

Said receptacle is hermetically closed during manufacture so that the scent of the air freshening product is fully retained, such that it is necessary to remove the hermetic closure or seal when said product is to be used.

One drawback of these air fresheners or systems for releasing volatile substances known today is that simply opening a receptacle or container cannot produce the desired dispersion of the scent of said air freshening product.

To overcome this drawback, systems for releasing volatile substances comprising a fan for generating an airflow for the correct dispersion of the scent of the air freshening product are already known.

In all these systems, the fragrance activating element or fan is located in a fixed position with respect to the receptacle of the volatile substances, the evaporation intensity being able to be changed by means of changing the work cycle or speed of the fan motor or by means of activating the opening fins.

These systems have an acceptable effectiveness for controlling the speed of evaporation of systems where the evaporation surface is fixed, such as systems with impregnated porous substrates, systems consisting of wicks or membranes. For systems where the evaporation surface moves as the volatile substance gradually evaporates, such as a container open to the air with a liquid or preferably a gel, the control obtained with these fixed fan systems is considerably less effective since the evaporation surface no longer coincides with the airflow.

Therefore, a first objective of the present invention is to provide a system for releasing volatile substances which allow improving and controlling the effectiveness of evaporation during work cycle.

SUMMARY OF THE INVENTION

The system for releasing volatile substances of the invention solves the mentioned drawbacks, having other advantages that will be described below.

The system for releasing volatile substances according to the present invention comprises:

a receptacle housing a volatile substance;
a ventilation surface arranged in said receptacle provided with ventilation windows; and
a fan for inducing the ventilation of the scent of said volatile substance,
and characterized in that said fan can move between at least a first position and a second position.

According to a preferred embodiment, said fan is assembled in a support pivoting with respect to said ventilation surface.

For example, in said first position, said fan can form a substantially 90° angle with respect to said ventilation surface, and in said second position said fan can form a substantially 45° angle with respect to said ventilation surface, such that the airflow strikes the inside of the container, which allows carrying the volatile substance in the head space of the container.

Advantageously, said support comprises at least one articulation for pivoting with respect to said ventilation surface.

According to a preferred embodiment, the receptacle is open and contains a volatile substance in liquid or gel form.

The effectiveness with which the perfume evaporates during the work cycle of the device can be improved and controlled with the system for releasing volatile substances according to the present invention.

BRIEF DESCRIPTION OF THE DRAWINGS

To better understand the preceding description, a set of drawings is attached in which a practical embodiment is schematically depicted by way of non-limiting example.

DETAILED DESCRIPTION OF THE INVENTION

Figure 1:
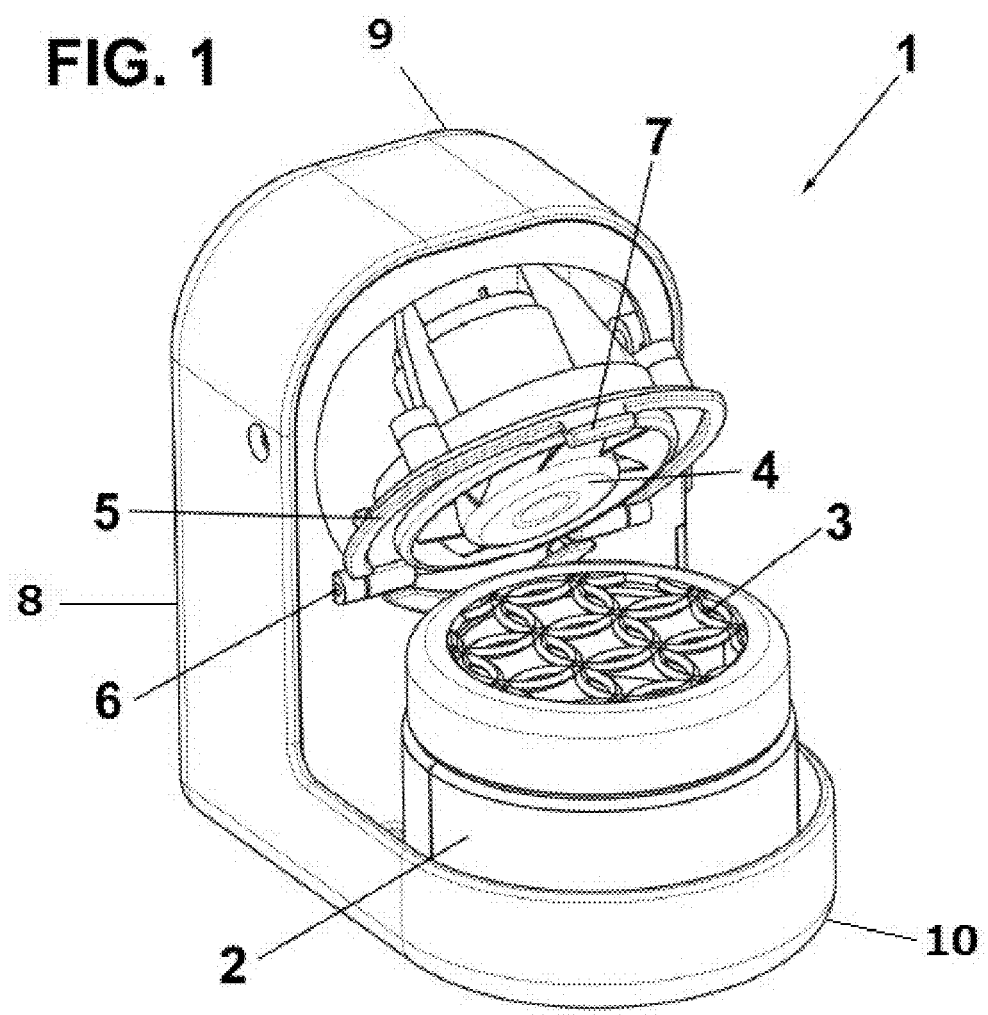
FIG. 1 is a perspective view of the system for releasing volatile substances of the present invention in a first position.

The system for releasing volatile substances according to the present invention is generally identified in the drawings by means of reference number 1, and comprises a receptacle 2 housing a volatile substance, for example, a scented gel.

Said receptacle 2 is closed at the upper portion thereof by means of, for example, a grid-like ventilation surface 3, preventing children from unintentionally accessing said volatile substance, for example.

It must be indicated that this receptacle 2 is a refill, such that it will be replaced in the system according to the present invention when the volatile substance no longer gives out any scent. In this manner, before use thereof, said receptacle 2 comprises a cover that is removed for use thereof, during which the volatile substance evaporates to the outside through said ventilation surface 3.

The system according to the present invention also comprises a fan 4 which increases the evaporation of said volatile substance, as will be described below.

Figure 2:
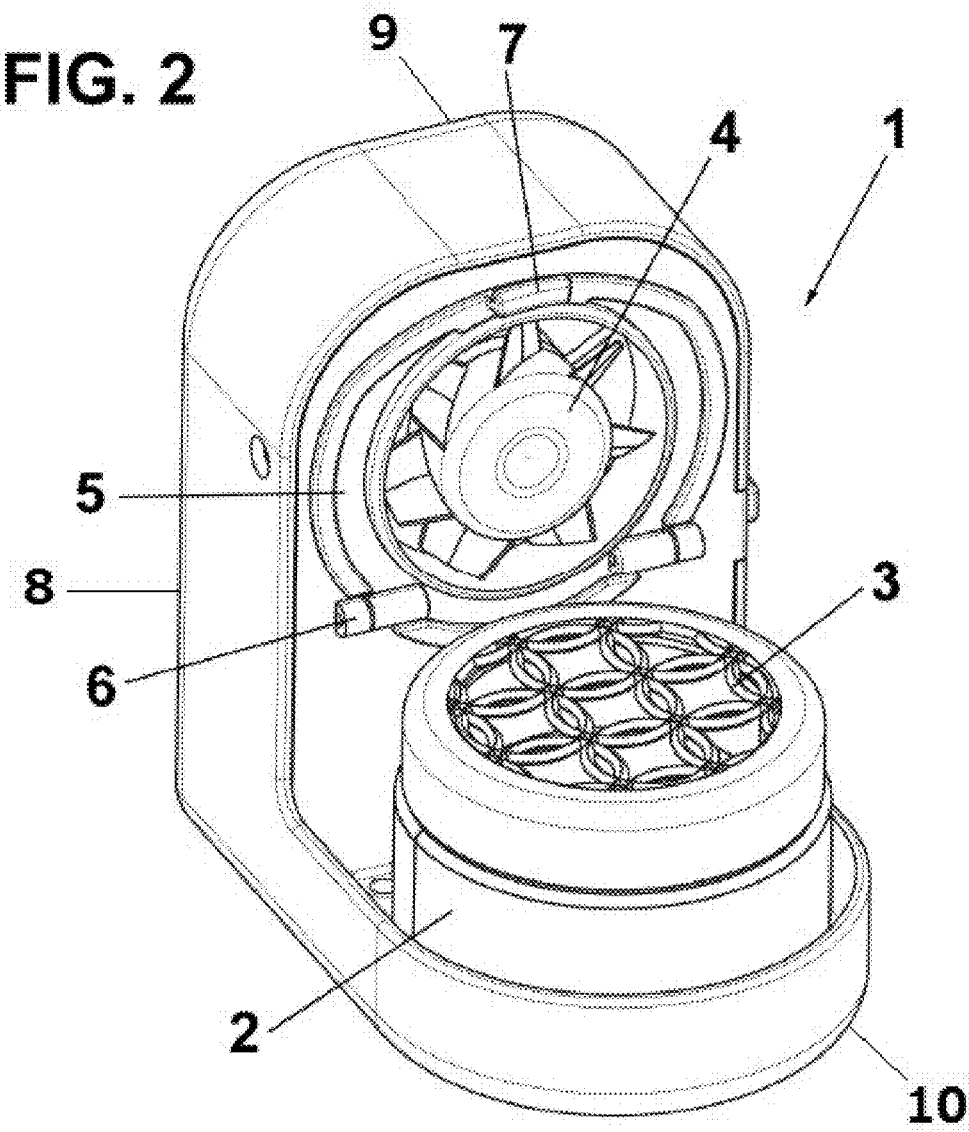
FIG. 2 is a perspective view of the system for releasing volatile substances of the present invention in a second position.

Said fan 4 is assembled in a support 5 which can pivot with respect to said ventilation surface 3, such that said fan 4 can be arranged in at least two different positions with respect to said ventilation surface 3, as can be seen in FIGS. 1 and 2.

Said support 5 pivots by means of, for example, a pair of articulations 6 located in the lower part of said support 5.

These articulations 6 allow the fan 4 to move a specific angle from a horizontal 0° position of the fan 4 (not depicted), to a vertical 90° position of the fan motor (depicted in FIG. 2, the optimum positions of the fan motor being 0° to 45° (depicted in FIG. 1).

With this change in the position of the fan 4, the effectiveness of the evaporation of the volatile substances during the work cycle of the device can be improved and controlled. The airflow strikes the volatile substances directly in the 45° position. In this position of the fan 4, the airflow enters through the mouth of the receptacle 2 and directly hits the surface of the volatile substances to be evaporated, thereby entraining the particles of the volatile substances in vapor state on the outermost surface of the volatile substance and speeds up the generation of new vapor, to again establish vapor equilibrium on the surface of the volatile substance, thereby increasing the evaporation of the fragrance contained in the receptacle 2.

In the 0° position of the fan 4, the airflow generated by the fan 4 passes right above the surface of the volatile substance. By increasing the speed of the air on the surface of the volatile substance, the atmospheric pressure thereof is reduced, and more vapor is therefore generated as a result of atmospheric pressure reduction on the surface of the volatile substance. The vapor generated by pressure reduction is spread by the airflow generated by the fan 4.

To prevent the user from being accustomed to the fragrance, the fan 4 can work permanently or in pulses. The user can choose one of these working modes as desired. In the specific case in which the fan 4 works in pulses, it will work between 5% and 50% of the time, the preferred working range being between 5% and 12.5% of the time. The time will be controlled by means of an electronic time controller.

The fan 5 can be an axial fan or any other type of fan. Furthermore, the fan 5 can be an axial fan with brushless motor, or can have an axial configuration with brushed motor, depending on the type of power supply source.

The position of the fan 4 is preferably changed in a manual manner. To that end, the support 5 is preferably made of a plastic material, for example, can comprise a pin 7 for fixing the fan 4 inside an upper portion 9 of the housing 8 thereof, as seen in FIG. 2, in which said fan is in a 90° position with respect to the ventilation surface 3.

To vary the position of the fan 4, the user will only need to pull the upper part of the support 5, in the area of the pin 7, so that the fan 4 is separated from its housing 8 having an upper portion 9 and a base portion 10.

Said support 5 can comprise any conventional stop element (not depicted) for arranging it in the 45° position depicted in FIG. 1, or the support 5 can be arranged in a 0° position (not depicted in the drawings) in which said fan 4 will be arranged on the ventilation surface 3 very close thereto.

Although reference has been made to a specific embodiment of the invention, it is obvious for a person skilled in the art that the system for releasing volatile substances described is susceptible to a number of variations and modifications, and that all the mentioned details can be replaced with other technically equivalent details without departing from the scope of protection defined by the attached claims.

What is claimed is:

1. A system for releasing volatile substances, comprising:
   a housing comprising a base portion and an upper portion,
   a receptacle equipped on the base portion of the housing, wherein the receptacle comprises a volatile substance;
   a ventilation surface arranged in said receptacle provided with ventilation windows; and
   a fan for inducing a ventilation of a scent of said volatile substance, wherein the fan is attached to the upper portion of the housing by an articulated hinge,
   wherein said fan is movable at least between a first position in which the fan forms a vertical angle 90° with respect to the ventilation surface and a second position in which the fan forms an angle 45° with respect to the ventilation surface by pivoting in the fan about said articulated hinge attached to the upper portion of the housing.

2. The system for releasing the volatile substances according to claim 1, wherein said fan is assembled in a support pivoting the fan with respect to said ventilation surface.

3. The system for releasing the volatile substances according to claim 1, wherein, said fan forms a substantially 90° angle with respect to said ventilation surface.

4. The system for releasing the volatile substances according to claim 1, wherein, said fan forms a substantially 45° angle with respect to said ventilation surface.

5. The system for releasing the volatile substances according to claim 1, wherein the receptacle is open and contains the volatile substance in liquid or gel form.

6. A method for releasing the volatile substance by the system of claim 1, wherein the method comprising:
   placing the receptacle comprising the volatile substance on the base portion of the housing;
   pivoting the fan about the articulated hinge to adjust the angle between 0° and 45° with respect to the ventilation surface; and
   causing an airflow entering the ventilation surface and evaporating the volatile substance.

7. The method of claim 6, further comprising:
   activating the fan intermittently.

8. The method of claim 7, wherein the fan is activated for a period of time between 5% and 50% relative to a period of time that the system is activated.

9. The method of claim 7, wherein the fan is activated for a period of time between 5% and 12.5% relative to a period of time that the system is activated.

\* \* \* \* \*

UNITED STATES PATENT AND TRADEMARK OFFICE
CERTIFICATE OF CORRECTION

| | |
|---|---|
| PATENT NO. | : 9,950,090 B2 |
| APPLICATION NO. | : 15/106255 |
| DATED | : April 24, 2018 |
| INVENTOR(S) | : Fernando Mayor Sans |

Page 1 of 1

It is certified that error appears in the above-identified patent and that said Letters Patent is hereby corrected as shown below:

In Column 3 at Line 4, Change "2," to --2),--.

In Column 4 at Line 22 (Approx.), In Claim 1, after "pivoting" delete "in".

Signed and Sealed this
Twenty-first Day of August, 2018

Andrei Iancu
*Director of the United States Patent and Trademark Office*